United States Patent [19]
Wantink

[11] Patent Number: 5,300,025
[45] Date of Patent: Apr. 5, 1994

[54] DILATATION CATHETER HAVING A COIL SUPPORTED INFLATION LUMEN

[75] Inventor: Kenneth L. Wantink, Murrieta, Calif.

[73] Assignee: Advanced Cardiovascular Systems, Inc., Santa Clara, Calif.

[21] Appl. No.: 954,477

[22] Filed: Sep. 30, 1992

[51] Int. Cl.$^5$ .............................................. A61M 29/00
[52] U.S. Cl. ..................................... 604/96; 604/282; 606/194
[58] Field of Search .................... 604/96, 102, 282; 606/192, 194; 128/772

[56] References Cited

U.S. PATENT DOCUMENTS

| | | | |
|---|---|---|---|
| 4,444,188 | 4/1984 | Bazell et al. | 606/194 |
| 4,684,363 | 8/1987 | Ari et al. | 604/98 |
| 4,917,666 | 4/1990 | Solar et al. | 604/95 |
| 5,156,594 | 10/1992 | Keith | 604/96 |
| 5,176,637 | 1/1993 | Sagae | 604/96 |
| 5,195,971 | 3/1993 | Sirhan | 604/96 |

Primary Examiner—C. Fred Rosenbaum
Assistant Examiner—Corrine Maglione
Attorney, Agent, or Firm—Crosby, Heafey, Roach & May

[57] ABSTRACT

A rapid exchange type dilatation catheter having a flexible distal portion which has a coil supported inflation lumen which is defined at least in part by an outer tubular member. An inner tubular member is disposed within the distal portion having a guidewire receiving inner lumen which extends proximally from a guidewire port in the distal end of the inner tubular member to a location proximal to an inflatable member on the distal portion of the catheter. The distal end of the relatively high strength proximal portion receives the proximal end of the support coil so as to provide a smooth transition.

8 Claims, 1 Drawing Sheet

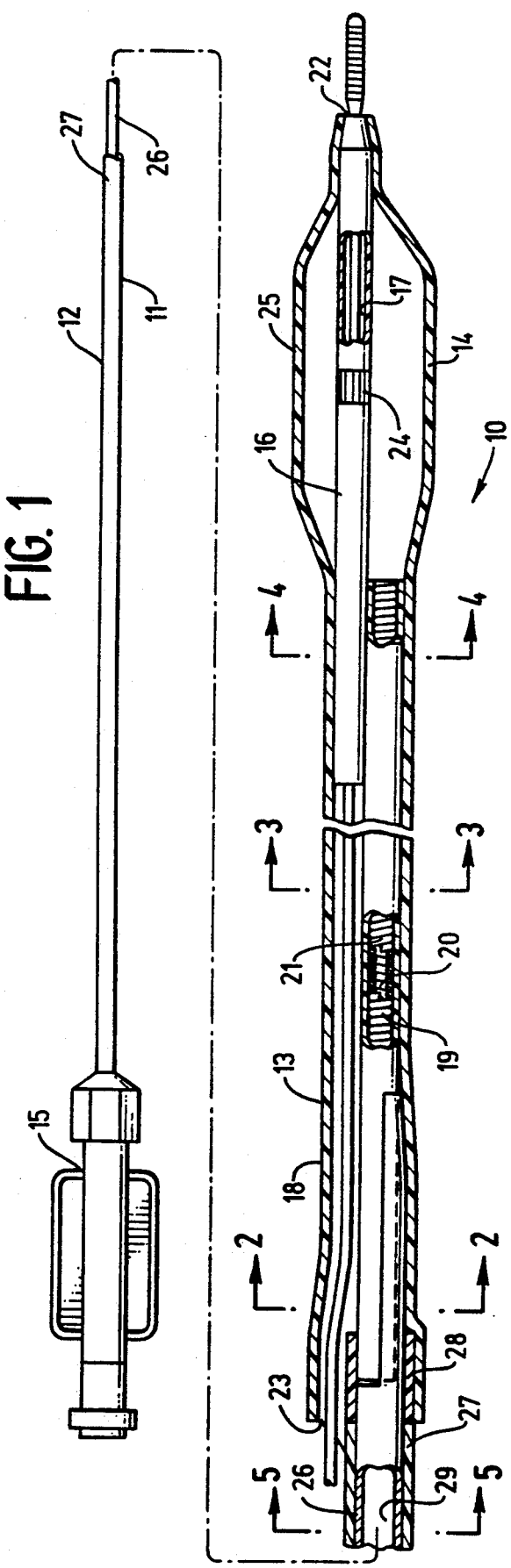
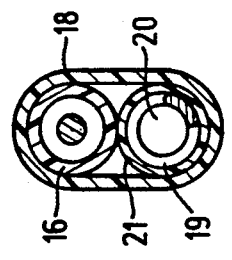
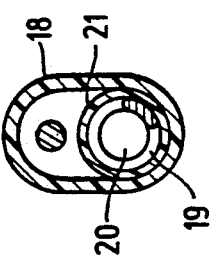
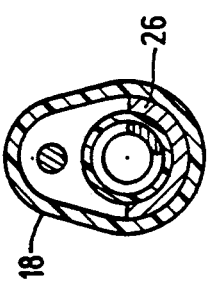
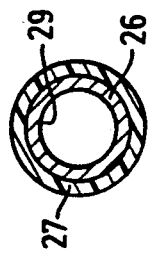

DILATATION CATHETER HAVING A COIL SUPPORTED INFLATION LUMEN

BACKGROUND OF THE INVENTION

This invention relates generally to intraluminal catheters, and more particularly to balloon dilatation catheters for performing angioplasty procedures.

In a PTCA procedure a guiding catheter having a preformed distal tip is first percutaneously introduced into the vascular system of a patient. The distal end of the guiding catheter is directed into the ostium or opening of the desired coronary artery and seated within the ostium by twisting or torquing the catheter from its proximal end which extends out of the patient.

A guidewire is advanced proximally through the guidewire lumen of the balloon catheter until only the distal tip of the guidewire extends out of the distal tip of the balloon catheter. The guidewire-balloon catheter assembly is inserted into the proximal end of the guiding catheter and advanced therethrough until the distal tip of the guidewire reaches the seated distal end of the guiding catheter.

The guidewire is then advanced out of the distal end of the guiding catheter and through the coronary artery until the distal tip of the guidewire is in position, typically several centimeters beyond the stenosis, to anchor the guidewire during the angioplasty procedure. Once the guidewire is in position, the balloon catheter is advanced out of the distal end of the guiding catheter over the guidewire until it reaches a desired location within the artery to be dilated, with the working section of the balloon traversing the stenosis to be dilated. Once in place across the stenosis, the balloon is inflated one or more times to compress the atherosclerotic plaque against the inside of the artery wall and to otherwise expand the artery. After inflation the balloon is then deflated so that blood flow is resumed through the now dilated artery and the dilatation catheter assembly and guiding catheter can be removed.

Further details of dilatation catheters, guidewires and devices associated therewith for angioplasty procedures may be found in the U.S. Pat. No. 4,323,071 to Simpson et al.; U.S. Pat. No. 4,439,185 to Lundquist; U.S. Pat. No. 4,468,224 to Enzmann et al.; U.S. Pat. No. 4,516,972 to Samson; U.S. Pat. No. 4,538,622 to Samson et al., U.S. Pat. No. 4,554,929 to Samson et al.; U.S. Pat. No. 4,616,652 to Simpson; U.S. Pat. No. 4,638,805 to Powell; U.S. Pat. No. 4,748,982 to Horzewski et al.; U.S. Pat. No. 4,748,986 to Morrison et al.; U.S. Pat. No. 4,821,722 to Miller et al.; and U.S. Pat. No. 4,898,577 to Badger et al. which are all hereby incorporated in their entirety by reference.

Another type of dilatation catheter is the rapid exchange type dilatation catheter, such as those available from the assignee of the present invention, Advanced Cardiovascular Systems, Inc., under the trademark ACS RX ® Coronary Dilatation Catheter. This catheter is described and claimed in U.S. Pat. No. 5,040,548 (Yock), U.S. Pat. No. 5,061,273 (Yock) and U.S. Pat. No. 4,748,982 (Horzewski et al,) and has a short guidewire receiving sleeve or inner lumen extending through the distal portion of the catheter. The sleeve preferably extends proximally a distance of at least about 10 cm and usually not more than about 50 cm from a first guidewire port in the distal end of the catheter to a second guidewire port in the catheter spaced proximally from the inflatable balloon of the catheter. A slit may be provided in the catheter wall which extends distally from the second guidewire port, preferably to a location proximal to the proximal end of the inflatable balloon to aid in the removal of the catheter from a guidewire. The structure of the catheter allows for the rapid exchange of the catheter without the need for the use of an exchange wire or adding a guidewire extension to the proximal end of the guidewire. The design of this catheter has been widely praised by the medical profession and has met with much commercial success in the market place because of its unique design.

A substantial improvement in the rapid exchange type dilatation catheters, such as described above, has recently been made by McInnes et al. which is described in copending applications Ser. No. 07/476,056, filed Feb. 7, 1990 and Ser. No. 07/541,264 filed Jun. 19, 1990, both entitled READILY EXCHANGEABLE PERFUSION DILATATION CATHETER, which are incorporated herein by reference. In this readily exchangeable dilatation catheter, perfusion ports are provided in the catheter shaft proximal and distal to the balloon which are in fluid communication with the guidewire receiving inner lumen to allow blood to perfuse distal to the catheter when the balloon was inflated.

In an angioplasty procedure with an over-the-wire dilatation catheter as discussed above, the balloon dilatation catheter is guided along the guidewire to the appropriate arterial location. However, if the catheter is too stiff longitudinally, it can fail to track over the guidewire and in some instances can pull the guidewire out of a branch of the artery.

If the catheter has insufficient radial stiffness, kinking can occur when the catheter traverses a turn but a portion of the catheter folds, i.e. kinks, instead of simply curving. Once a kink occurs, it prevents any further pushing force from being applied to the catheter and it can limit the flow of fluid through the catheter which is necessary for inflation of the catheter.

Thus, it is advantageous to have an over-the-wire catheter which has sufficient longitudinal flexibility to negotiate the curves and to track well over a guidewire in the vascular system but which is sufficiently radially rigid to prevent kinking. The catheter of the present invention provides such advantages.

SUMMARY OF THE INVENTION

The present invention is directed to an improved rapid exchange type dilatation catheter.

The rapid exchange type dilatation catheter of the invention generally includes an elongated catheter shaft with a relatively stiff proximal portion which has an inflation lumen extending therein and a more flexible distal section which has a coil supported inflation lumen and a guidewire receiving inner lumen and an inflatable member or balloon on the flexible distal section of the catheter shaft which has an interior in fluid communication with the inflation lumen within the proximal portion through a coil supported inflation lumen which extends through the distal section of the catheter shaft.

In a presently preferred embodiment the flexible distal section has an outer tubular member, a portion of which in conjunction with the supporting coil defines the inflation lumen extending through the distal section. The distal section also has an inner tubular member with proximal and distal ends and guidewire receiving inner lumen. The inner tubular member extends proximally from the distal end of the distal section, through the interior of the balloon and beyond the proximal end of the balloon. The inner tubular member may extend to the proximal end of the distal section or the proximal extension thereof may terminate short of the proximal end of the distal section. In the latter case the outer tubular member forms the remainder of the guidewire receiving inner lumen. To provide a smoother transition at the junction between the proximal and distal sections of the catheter shaft the outer tubular member extends proximally beyond the distal end of the proximal portion of the catheter shaft.

The catheter of the invention provides very low profile while maintaining radial stiffness which prevents kinking and longitudinal flexibility which facilitates tracking. The relatively stiff proximal section ensures adequate pushability. These and other advantages of the invention will become more apparent from the following detailed description of the invention when taken in conjunction with the accompanying drawings.

BRIEF DESCRIPTION OF THE DRAWINGS

FIG. 1 is an elevational view, partially in section, of the catheter embodying features of the present invention.

FIG. 2 is a transverse cross-sectional view of the catheter illustrated in FIG. 1 taken along lines 2—2.

FIG. 3 is a transverse cross-sectional view of the catheter illustrated in FIG. 1 taken along lines 3—3.

FIG. 4 is a transverse cross-sectional view of the catheter illustrated in FIG. 1 taken along lines 4—4.

FIG. 5 is a transverse cross-sectional view of the catheter illustrated in FIG. 1 taken along lines 5—5.

DETAILED DESCRIPTION OF THE INVENTION

Reference is made to a presently preferred embodiment of the invention which is illustrated in FIGS. 1-5. As shown in these drawings, catheter 10 includes an elongated catheter shaft 11 which has an elongated relatively stiff proximal section 12 and a relatively short distal section 13, an inflatable member or balloon 14 which is disposed about the distal section and an adapter 15 which is mounted on the proximal end of the proximal section 12. The distal section 13 is provided with an inner tubular member 16 having a guidewire receiving inner lumen 17. An outer tubular member 18 extends proximally from the proximal end of the balloon and is provided with a support coil 19 to define an inflation lumen 20. An outer sheath 21 formed of suitable thermoplastic material such as polyethylene sealingly engages the coil 19. The support coil 20 and the inner tubular member 16 are coextensive over part of their lengths and are generally parallel and offset from each other. The guidewire receiving inner lumen 17 within the inner tubular member 16 extends from a distal guidewire port 22 in the distal end of the inner tubular member to a proximal guidewire port 23 located at or near the junction between the proximal and distal sections 12 and 13 respectively.

Balloon 14 has a distal end which is secured to the distal end of inner tubular member 16 and a proximal extension which forms the outer tubular member 18. The balloon 14 and the outer tubular member 18 may be members which have been formed separately and secured together or they may be formed together from a single plastic tubular member. A radiopaque marker 24 is disposed about the exterior of the inner tubular member 16 at a position which indicates the midpoint of the working section 25 of the balloon 14 to facilitate its fluoroscopic observation within a patient.

The proximal section 12 of the catheter shaft 11 includes a tubular element 26 formed of a high strength material such as 304 stainless steel or Nickel-Titanium alloy, commonly referred to as NiTi, hypotubing and an outer jacket or coating 27 formed of a thermoplastic material, e.g. polyethylene, which is heat shrunk to fit over inner tubular element. As illustrated in FIG. 1, a portion of the distal extremity of the inner tubular element 26 is cut away to accept the proximal end of the support coil 20. The proximal end of the coil 19 and the distal end of the inner tubular element 26 are secured together by a short tubular heat shrunk plastic element 28 which extends over the coil in the cut-away portion and the uncut-away portions of the tubular element 26 to join these elements together and sealingly interconnect the inflation lumen 21 in the distal section 13 with the inner lumen 29 extending within the tubular element 26.

The coupling of tubular element 26 and support coil 19 provides a smooth transition between the proximal and distal sections 12 and 13, respectively, and minimizes the possibility that the distal section will kink when it is advanced through a patient's coronary anatomy.

The proximal end of the outer tubular member 18 extends proximally beyond the junction between the proximal and distal sections 12 and 13 of the catheter shaft 11 and is expanded as shown to form the proximal guidewire port 23. The portion of the outer tubular member 18 which defines in part the guidewire receiving lumen 17 proximal to the proximal end of the inner tubular member 16 may be formed by heat shrinking the portion of the outer tubular member 18 which surrounds support coil 19 while a mandrel with an exterior in a desired shape is maintained parallel and offset from the support coil. Upon cooling the mandrel is removed, leaving the guidewire lumen 17 defined in the desired shape.

During an angioplasty procedure proximal guidewire port 23 should be located inside the inner lumen of the guiding catheter to ensure that the guidewire extends outside of the dilatation catheter within the guiding catheter lumen. The proximal guidewire port 23 is disposed proximal to balloon 14 in a rapid exchange type catheter which allows the in-place catheter to be removed without moving the guidewire.

Generally the various components of the catheter of the invention may be formed of conventional materials. For example, the balloon 14, the inner tubular member 16 and the outer tubular member 18 may be formed of polyethylene plastic of varying densities. The radiopaque marker 24 is opaque to whatever radiation is being used to image the location of the center of balloon 14, e.g. gold. Support coil 19 may be formed from stainless steel wire which is coiled tightly.

In a typical catheter in accordance with the invention the length of the catheter shaft from adaptor to the distal end is about 135 cm. The proximal guidewire port 23 is located at least about 10 cm but not more than about 50 cm from the distal end of the catheter. The inner tubular member is about 4 to about 20 cm in length with a diameter of about 0.016 to about 0.025 inch. The support coil is about 8 to about 40 cm long with an outer diameter of about 0.005 to about 0.01 inch.

One of the advantages in using support coil 19 within the inflation lumen is the ease of manufacture of the catheter. In the portions of the outer tubular member in which the support coil does not extend, a mandrel is used to maintain a passage for the inflation port during fusing of the outer tubular member 18 to the inner tubular member 16 around a portion thereof.

It will be apparent to those skilled in the art that various modifications and improvements can be made to the present invention without departing from the scope of the invention. As an example, the guidewire lumen may be extended to run the entire length of the catheter so that the catheter is a standard over-the-wire catheter instead of the rapid exchange catheter described herein.

What is claimed is:

1. An intravascular catheter having an elongated shaft with proximal and distal portions, an inflatable member on the distal portion of the shaft and an inflation lumen extending within the shaft which is in fluid communication with the interior of the inflatable member, the distal portion of the elongated shaft comprising:
   a) an inner tubular member having an exterior surface, proximal and distal ends and a guidewire receiving lumen extending from a guidewire port in the distal end thereof to a guidewire port spaced proximally from the inflatable member, with a distal end of the inflatable member sealingly secured about the distal end of the inner tubular member;
   b) an outer tubular member disposed about the inner tubular member and defining at least in part the inflation lumen extending within the distal portion of the elongated shaft separate and offset from the inner tubular member; and
   c) a support coil, having an exterior surface, which is disposed within the the inflation lumen in the distal portion of the elongated shaft and which is separate and completely offset from the inner tubular member such that the exterior surface of the coil is adjacent to the exterior surface of the inner tubular member.

2. A balloon dilatation catheter having an elongated shaft with proximal and distal portions, an inflatable member on the distal portion of the shaft and an inflation lumen extending within the shaft which is in fluid communication with the interior of the inflatable member, the distal portion of the elongated shaft comprising:
   a) an inner tubular member having an exterior surface, proximal and distal ends and a guidewire receiving lumen extending from a guidewire port in the distal end thereof to a guidewire port spaced proximally from the inflatable member, with a distal end of the inflatable member sealingly secured about the distal end of the inner tubular member;
   b) an outer tubular member disposed about the inner tubular member and defining at least in part the inflation lumen extending within the distal portion of the elongated shaft which is parallel to and offset from the inner tubular member; and
   c) a coiled, having an exterior surface support member disposed within the part of the inflation lumen which is disposed in the distal portion of the elongated shaft and which is separate and completely offset from the inner tubular member such that the exterior surface of the coil is adjacent to the exterior surface of the inner tubular member.

3. The balloon dilatation catheter of claim 2 wherein the proximal portion of the catheter shaft is formed of high strength tubing with proximal and distal ends and with the inflation lumen extending therein.

4. The balloon dilatation catheter of claim 3 wherein the high strength tubing is hypotubing.

5. The balloon dilatation catheter of claim 3 wherein the distal end of the high strength tubing is adapted to receive a proximal portion of the coiled support member.

6. The balloon dilatation catheter of claim 3 wherein the outer tubular member has a proximal end secured to the distal end of the high strength tubing.

7. The balloon dilatation catheter of claim 3 wherein the high strength tubing has a proximal end provided with an adapter which directs inflation fluid into the inflation lumen within the high strength tubing.

8. The balloon dilatation catheter of claim 4 wherein the hypotubing is provided with a plastic jacket on the exterior thereof.

* * * * *